United States Patent
Metz

(10) Patent No.: US 10,511,068 B2
(45) Date of Patent: Dec. 17, 2019

(54) PROCESS FOR RECOVERING AN ELECTROLYTE SALT

(71) Applicant: RHODIA OPERATIONS, Paris (FR)

(72) Inventor: François Metz, Irigny (FR)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 15/318,119

(22) PCT Filed: Jun. 16, 2015

(86) PCT No.: PCT/EP2015/063381
§ 371 (c)(1),
(2) Date: Dec. 12, 2016

(87) PCT Pub. No.: WO2015/193261
PCT Pub. Date: Dec. 23, 2015

(65) Prior Publication Data
US 2017/0110769 A1    Apr. 20, 2017

(30) Foreign Application Priority Data
Jun. 18, 2014 (FR) .................... 14 01375

(51) Int. Cl.
| | | |
|---|---|---|
| C07F 1/02 | (2006.01) |
| H01M 10/54 | (2006.01) |
| B01D 11/02 | (2006.01) |
| B01D 11/04 | (2006.01) |
| H01M 6/52 | (2006.01) |
| H01M 10/0568 | (2010.01) |
| B01D 3/14 | (2006.01) |
| H01M 10/0569 | (2010.01) |

(52) U.S. Cl.
CPC ............ *H01M 10/54* (2013.01); *B01D 3/14* (2013.01); *B01D 11/02* (2013.01); *B01D 11/0288* (2013.01); *B01D 11/0292* (2013.01); *B01D 11/04* (2013.01); *B01D 11/0492* (2013.01); *C07F 1/02* (2013.01); *H01M 6/52* (2013.01); *H01M 10/0568* (2013.01); *H01M 10/0569* (2013.01); *H01M 2300/0031* (2013.01); *Y02W 30/84* (2015.05)

(58) Field of Classification Search
None
See application file for complete search history.

(56) References Cited

U.S. PATENT DOCUMENTS

| | | | |
|---|---|---|---|
| 6,433,227 B1 | 8/2002 | Buchholz et al. | |
| 8,753,594 B1 * | 6/2014 | Burba, III | C01D 15/00 423/179.5 |

FOREIGN PATENT DOCUMENTS

| | | |
|---|---|---|
| EP | 2410603 A1 | 1/2012 |
| FR | 2868603 A1 | 10/2005 |
| JP | H0517832 A1 | 1/1993 |
| JP | 2001-518393 A | 10/2001 |
| JP | 2005-515605 A | 5/2005 |
| JP | 5360328 B1 | 12/2013 |
| WO | 03/061056 A1 | 7/2003 |
| WO | 2008022415 A1 | 2/2008 |

OTHER PUBLICATIONS

Haynes et al. (CRC Handbook of Chemistry and Physics, 94 Ed., 2014, Section 15: Practical Laboratory Data, Laboratory Solvents and Other Liquid Reagents).*

* cited by examiner

*Primary Examiner* — Sudhakar Katakam
*Assistant Examiner* — Jennifer C Sawyer

(57) ABSTRACT

The present invention relates to a process for recovering a metal salt of an electrolyte dissolved in a matrix, said process consisting in subjecting the electrolyte to a liquid extraction with water.

14 Claims, No Drawings

PROCESS FOR RECOVERING AN ELECTROLYTE SALT

This application is a U.S. national phase entry under 35 U.S.C. § 371 of International Application No. PCT/EP2015/063381, filed on Jun. 16, 2015, which claims priority to French Application No. 14/01375, filed on Jun. 18, 2014. The entire contents of these applications are explicitly incorporated herein by this reference.

The present invention relates to a process for recovering a metal salt, in particular a lithium salt, contained in an electrolyte.

Sulfonimide salts, such as lithium bis(trifluoromethanesulfonyl)imide (($CF_3SO_2$)$_2$NLi or LiTFSI), lithium bis(fluorosulfonyl)imide (($SO_2F$)$_2$NLi or LiFSI) or lithium bis(perfluoroethanesulfonyl)imide (($C_2F_5SO_2$)$_2$NLi), are compounds of particular interest. They in particular have properties that make them valuable compounds for electronic applications that are demanding as regards purity and quality, for example the conduction and/or the dissipation of electronic charges in the battery or antistatic markets or in electrochromism. These compounds are in particular used in an electrolyte and are, in this case, in a matrix which may be a polymer, a gel or an organic solvent.

Processes for recycling electrolytes exist in the prior art. These processes are, however, generally focused on the recovery of the metal, in particular of lithium, which is expensive, and not on the recovery of the salt of the metal per se, or even on the recovery of the matrix of the electrolyte (which is a solvent in the case of a liquid electrolyte), even though these variants nevertheless have not insignificant advantages in terms of cost and preservation of the environment.

Thus, application WO 2008/022415 describes a process for recovering lithium from the electrolyte of a lithium battery, according to which a spent battery is brought into contact with a solution of ethanol containing 5% of acetone and, after extraction of the lithium salt and chemical reaction thereof with various constituents of the medium, the lithium is recovered in the form of $Li_2CO_3$. The filtrate is then distilled so as to recover ethanol which may be used for a new extraction. In such a process, only the lithium is recovered, and said lithium is in a modified chemical form which means that it cannot be re-used as it is in a lithium battery.

Patent application FR 2 868 603 also describes a process for treating lithium-anode cells and batteries. Besides lithium, said document proposes only the recovery of the $PF_6$ anion. Patent application JP H05-017832 also provides a process for recovering the lithium contained in a lithium battery, but proposes no means for recovering the lithium salt anion. The objective of the present invention is to provide a process for recovering metal salts of electrolytes, especially lithium salts, in particular lithium sulfonimides and especially ($CF_3SO_2$)$_2$NLi, which causes little or no modification of the chemical nature of the metal salt and which also optionally makes it possible to recover the matrix of the electrolyte, whether it is in the form of a polymer, of a gel or of a solvent.

To this effect, the present invention relates to a process for recovering a metal salt of an electrolyte dissolved in a matrix, said process consisting in subjecting the electrolyte to a liquid extraction with water.

The term "metal salt" is intended to mean an organic or inorganic salt of a metal, preferably of an alkali metal, in particular selected from: K, Na or Cs. Lithium (Li) salts are particularly preferred.

In the process according to the invention, the metal salt may be selected from the group consisting of sulfonimides, perchlorates, sulfonates, difluorophosphates and mixtures thereof.

Preference is given to sulfonimides having the formula ($Rf^1SO_2$)($Rf^2SO_2$)$NM^b$, $M^b$ representing an alkali metal, in particular selected from: K, Li, Na and Cs, $Rf^1$ and $Rf^2$ independently representing a fluorine atom or a group having from 1 to 10 carbon atoms, selected from fluoroalkyls, perfluoroalkyls and fluoroalkenyls.

Within the context of the invention:
- the term "alkyl" is intended to mean a linear or branched hydrocarbon-based chain preferably comprising from 1 to 10 carbon atoms, in particular from 1 to 4 carbon atoms;
- the term "fluoroalkyl" is intended to mean a group formed from a linear or branched $C_1$-$C_{10}$ hydrocarbon-based chain comprising at least one fluorine atom;
- the term "perfluoroalkyl" is intended to mean a group formed from a linear or branched $C_1$-$C_{10}$ chain comprising only fluorine atoms, in addition to the carbon atoms, and devoid of a hydrogen atom;
- the term "fluoroalkenyl" is intended to mean a group formed from a linear or branched $C_1$-$C_{10}$ hydrocarbon-based chain comprising at least one fluorine atom and comprising at least one double bond.

Preferably, the $Rf^1$ and $Rf^2$ groups are independently selected from a fluorine atom or a group having from 1 to 5 carbon atoms, selected from fluoroalkyls, perfluoroalkyls and fluoroalkenyls.

The metal salt may preferably be selected from lithium bis(trifluoromethanesulfonyl)imide, lithium bis(fluorosulfonyl)imide or lithium bis(perfluoroethanesulfonyl)imide, preferably lithium bis(trifluoromethanesulfonyl)imide.

The metal salt may also be selected from $LiClO_4$ (lithium perchlorate) and LiOTf (lithium trifluoromethanesulfonate, also called lithium triflate).

The metal salt may also be $LiPO_2F_2$ (lithium difluorophosphate).

Moreover, it is indicated herein that the inorganic lithium salts may be selected from $LiPF_6$, $LiBF_4$, $LiClO_4$, $LiAsF_6$ or lithium borates and phosphates. The organic lithium salts are preferably selected from the fluoroalkyl variants of the abovementioned borates and phosphates, LiOTf (or lithium trifluoromethanesulfonate) or the abovementioned lithium sulfonimides, for example lithium bis(trifluoromethanesulfonyl)imide (($CF_3SO_2$)$_2$NLi or LiTFSI), lithium bis(fluorosulfonyl)imide (($SO_2F$)$_2$NLi or LiFSI) or lithium bis(perfluoroethanesulfonyl)imide (($C_2F_5SO_2$)$_2$NLi), in particular LiTFSI.

The term "electrolyte" is intended to mean a medium containing ions which make it conductive, i.e. which allows an electric current to pass through. This medium may be solid or liquid. According to the invention, the ions are provided by the metal salt and said salt is dissolved in a non-conductive matrix which may be a polymer, a gel or an organic solvent.

According to the invention, the extraction takes place by bringing into contact with water, preferably at atmospheric pressure and at a temperature of between 0 and 100° C., preferably between 20 and 60° C. The extraction solvent therefore contains at least water. An aqueous extraction solution is obtained, said solution containing at least a part of the metal salt.

In a first variant of the invention, the matrix comprises a polymer or a gel in which the metal salt is dissolved, i.e. the metal salt has not chemically reacted with said matrix. The polymer contained in the matrix may, for example, be POE (polyethylene oxide) or a silicone oil. The gel contained in the matrix may, for example, be PAN (polyacrylamides), the PVDF (PolyVinylideneDiFluoride) homopolymer or a VDF (vinylidene fluoride)-HFP (hexafluoropropylene) copolymer.

In this variant, at the end of the liquid extraction step with water, on the one hand the polymer or the gel and, on the other hand, an aqueous solution containing at least a part of the metal salt are generally recovered. The polymer or the gel may optionally be re-used in the same application, as electrolyte, optionally after an appropriate treatment, involving, for example, drying.

In a second variant of the invention, the matrix of the electrolyte comprises an organic solvent. In this variant, the solution of the metal salt in the organic solvent (i.e. the electrolyte) is miscible with water, and this electrolyte may be successively or simultaneously subjected to a liquid extraction with water and with an organic extraction solvent which is water-immiscible.

In this variant, the steps of extraction with water and with the organic solvent may be carried out in any order. Preferably, the aqueous extraction is carried out first. Indeed, generally, spent devices comprising an electrolyte are ground in the presence of water, for example under water or in the presence of a water mist, thereby making it possible to eliminate the heat emitted by the grinding and to avoid any risks of sparks.

The organic solvent of the electrolyte should ideally have a good compromise between two antagonistic properties, namely: a high electric constant and a low boiling point (corresponding to a high fluidity). It is preferably at least one and preferably at least two solvent(s) selected from aliphatic sulfones, such as DMSO (dimethyl sulfoxide), DESO (diethyl sulfoxide), DPSO (dipropyl sulfoxide), EMS (ethylmethyl sulfoxide), or FEMS (fluroroethylmethyl sulfoxide); alkyl carbonates, such as PC (propyl carbonate), EC (ethyl carbonate) or DMC (dimethyl carbonate); nitriles, such as AdN (adiponitrile) and MGN (methylglutaronitrile); and GBL (γ-butyrolactone).

A mixture of at least two solvents generally makes it possible to more easily achieve the compromise of above-mentioned properties. Good results have in particular been obtained with the EC/DMC mixture.

The choice of the organic extraction solvent which is water-immiscible depends in particular on the solvent of the electrolyte, and those skilled in the art will be able to easily identify it on the basis of the solvent miscibility tables available in the literature. It should be noted that the extraction solvent may also be a mixture of solvents. Chlorinated solvents such as chloroform, dichloroethane and perchloroethylene are very suitable. Good results have been obtained with methylene chloride and/or chlorobenzene, in particular when the electrolyte comprises an EC/DMC mixture.

The extraction step with the organic solvent is preferably carried out at ambient pressure and temperature.

At the end of the two liquid/liquid extractions, two liquid phases are present: an aqueous phase in which substantially all the metal salt is dissolved and an organic phase containing substantially all the organic solvent of the electrolyte and the organic extraction solvent.

The term "substantially" is intended to mean at least 70%, preferably at least 80%, or even at least 90% of the initial amount present in the medium treated (either a spent, preferably ground, device, or an aqueous solution obtained by aqueous extraction thereof).

Preferably, these two phases are separated, for example by settling out or centrifugation.

In practice, the two variants above are often combined since, industrially, a mixed stream of devices including both solid electrolytes and liquid electrolytes is generally treated and, consequently, in order to extract the metal salt therefrom, it is first necessary to carry out an extraction with water. In the case where the treated stream also comprises liquid electrolyte, the liquid phase(s) resulting from the extraction with water is (are) then preferably subjected to an extraction with a water-immiscible organic solvent.

According to one preferred variant of the invention, one or each of these phases may be treated so as to recover therefrom respectively the metal salt and the solvent of the starting electrolyte.

Within the context of the invention, the term "miscible with" is intended to mean generally soluble at at least 5% by weight, or even at at least 10% by weight.

The term "immiscible" is intended to mean generally miscible at less than 5% by weight, preferably at less than 2% by weight.

The term "liquid extraction" is intended to mean bringing into contact with water or the solvent in an amount and for a period sufficient to extract therefrom respectively a substantial amount of the solvent or of the metal salt, i.e. at least 70%, preferably at least 80%, or even at least 90% by volume of the initial amount present in the medium treated. The water or the solvent used may be substantially pure, preferably at least 70% by volume, preferably at least 80%, or even at least 90% pure. The ratio by volume of water or of liquid relative to the medium to be extracted may be between 20:80 and 80:20, preferably between 40:60 and 60:40. The duration of the bringing into contact may be, for example, at least 0.5 hour.

According to the invention, the liquid extraction may be carried out in a single step or it may be carried out in several successive steps, i.e. it may be staged. Generally, the extraction with water is carried out in a single step. On the other hand, the extraction with the organic solvent, where appropriate, is advantageously staged. In this case, preferably, at least 20% by volume of the organic solvent of the electrolyte is extracted in the first step, and as many steps as are necessary are preferably used to extract in total at least 90% of the solvent.

In a first preferred variant of the invention, the aqueous solution containing the metal salt is dried, for example by spray-drying, so as to extract therefrom the directly re-usable metal salt. This variant is very suitable in the case of aqueous solutions which are sufficiently pure, i.e. which make it possible to obtain metal salts of which the purity is sufficient for the intended use (for example: re-use in an electrolyte).

In a second preferred variant of the invention, the metal salt is LiTFSI and the aqueous solution containing it is preferably first concentrated, for example by evaporation, distillation or lyophilization. This solution is then acidified so as to generate HTFSI, which is preferably first purified (for example by distillation, etc) and then brought into contact again with an aqueous solution of fresh LiOH or $Li_2CO_3$, so as to regenerate the LiTFSI. In other words, the aqueous extraction solution containing LiTFSI is acidified so as to generate HTFSI and $LiHSO_4$ which are isolated, and then the HTFSI is brought into contact with fresh LiOH or $Li_2CO_3$ so as to regenerate the LiTFSI.

In a third preferred variant of the invention, which applies only to the case of liquid electrolytes also subjected to extraction with an organic solvent, the organic phase containing the solvent(s) of the electrolyte and the extraction solvent is treated so as to separate the solvents, for example by distillation. The solvents thus regenerated can optionally, as a result of additional treatment(s), also be re-used, preferably in the same application, i.e. respectively as electrolyte solvent and as extraction solvent.

The examples that follow may illustrate the invention without, however, limiting it.

EXAMPLE 1

A synthetic electrolyte was obtained by incorporating LiTFSI (1 M) into an EC/DMC mixture at 50% by volume of each of the two solvents.

The resulting solution was extracted with an equivalent volume of methyl chloride, and then with an equivalent volume of water. Two phases, easy to separate by settling out, were obtained, the LiTFSI being at more than 95% by weight in the aqueous phase.

EXAMPLE 2

The conditions were identical to example 1, but with chlorobenzene as organic extraction solvent, for a similar result.

COUNTEREXAMPLE

The conditions were identical to example 1, but with MEK (methyl ethyl ketone) as extraction solvent, but said solvent did not make it possible to obtain two distinct phases easy to separate by settling out.

EXAMPLE 3

A spent flexible battery weighing in total 34 g and comprising 2 g of LiTFSI in solution in an EC/DMC mixture was subjected to a single-step extraction with 600 g of water and 900 g of methylene chloride. Two phases, easy to separate by settling out, were obtained, and 1.8 g i.e. 90% of the LiTFSI in the aqueous phase were recovered.

The invention claimed is:

1. A process for recovering a metal salt, wherein the metal salt is selected from the group consisting of potassium, lithium, and sodium sulfonimides, of an electrolyte dissolved in a matrix, said process consisting in subjecting the electrolyte to a liquid extraction with water when the matrix comprises a polymer or a gel, and when the matrix of the electrolyte comprises an organic solvent, the electrolyte is successively or simultaneously subjected to a liquid extraction with water and with a chlorinated organic extraction solvent which is water-immiscible, wherein the ratio by volume of water relative to the organic solvent and/or chlorinated organic extraction solvent is between 20:80 and 80:20, and recovering substantially all the metal salt dissolved in the aqueous phase.

2. The process as claimed in claim 1, wherein the metal salt is a lithium salt.

3. The process as claimed in claim 1, wherein the metal salt is a sulfonimide having the formula $(Rf^1SO_2)(Rf^2SO_2)NM^b$, $M^b$ representing potassium, lithium, or sodium, $Rf^1$ and $Rf^2$ independently representing a fluorine atom or a group having from 1 to 10 carbon atoms.

4. The process as claimed in claim 3, wherein the metal salt is lithium bis(trifluoromethanesulfonyl)imide, lithium bis(fluorosulfonyl)imide or lithium bis(perfluoroethanesulfonyl)imide.

5. The process as claimed in claim 4, wherein the metal salt is lithium bis(trifluoromethanesulfonyl)imide.

6. The process as claimed in claim 1, wherein, at the end of the two liquid extractions, two liquid phases are present: an aqueous phase in which substantially all the metal salt is dissolved and an organic phase containing substantially all the organic solvent of the electrolyte and the organic extraction solvent, and these two phases are separated.

7. The process as claimed in claim 6, wherein the organic phase containing the solvent(s) of the electrolyte and the extraction solvent is treated so as to separate the solvents.

8. The process as claimed in claim 1, wherein an aqueous extraction solution containing the metal salt obtained by subjecting the electrolyte to the liquid extraction with water is dried, so as to extract therefrom the metal salt.

9. The process as claimed in claim 1, wherein the metal salt is LiTFSI and the aqueous extraction solution containing the LiTFSI is acidified so as to generate HTFSI and LiOH which are isolated and then brought into contact with one another again so as to regenerate the LiTFSI.

10. The process as claimed in claim 3, wherein the group having from 1 to 10 carbon atoms is selected from the group consisting of fluoroalkyls, perfluoroalkyls and fluoroalkenyls.

11. The process as claimed in claim 1, wherein the chlorinated solvent is chloroform, dichloroethane, perchloroethylene, methylene chloride and/or chlorobenzene.

12. The process as claimed in claim 6, wherein the two phases are separated by settling out or by centrifugation.

13. The process as claimed in claim 7, wherein the organic phase containing the solvent(s) of the electrolyte and the extraction solvent is treated so as to separate the solvents by distillation.

14. The process as claimed in claim 1, wherein the ratio by volume of water relative to the organic solvent and/or chlorinated organic extraction solvent is between 40:60 and 60:40.

* * * * *